(12) United States Patent
Garcia Perez et al.

(10) Patent No.: US 10,945,645 B2
(45) Date of Patent: Mar. 16, 2021

(54) DEVICE FOR SAMPLING ONE OR MORE ANALYTES

(71) Applicant: GlucoModicum Oy, Helsinki (FI)

(72) Inventors: Alejandro Garcia Perez, Helsinki (FI); Heikki Nieminen, Helsinki (FI); Edward Haeggström, Helsinki (FI)

(*) Notice: Subject to any disclaimer, the term of this patent is extended or adjusted under 35 U.S.C. 154(b) by 228 days.

(21) Appl. No.: 16/324,570

(22) PCT Filed: Nov. 8, 2017

(86) PCT No.: PCT/FI2017/050767
§ 371 (c)(1),
(2) Date: Feb. 11, 2019

(87) PCT Pub. No.: WO2018/091771
PCT Pub. Date: May 24, 2018

(65) Prior Publication Data
US 2019/0175081 A1    Jun. 13, 2019

(30) Foreign Application Priority Data

Nov. 21, 2016 (FI) ................................ 20165876

(51) Int. Cl.
*A61B 5/1477* (2006.01)
*A61B 5/1486* (2006.01)
(Continued)

(52) U.S. Cl.
CPC ........ *A61B 5/14514* (2013.01); *A61B 5/0002* (2013.01); *A61B 5/1477* (2013.01); *A61B 5/1486* (2013.01); *A61B 5/14532* (2013.01); *A61B 5/14546* (2013.01); *A61B 5/150022* (2013.01); *A61B 5/150091* (2013.01);
(Continued)

(58) Field of Classification Search
CPC ................. B01D 15/30; B01D 15/327; A61K 39/39591; C07K 16/00; C07K 16/065; C07K 16/10; C07K 16/06; G01N 30/02; G01N 33/6854; G01N 2030/027;
(Continued)

(56) References Cited

U.S. PATENT DOCUMENTS

2002/0002328 A1*  1/2002  Tamada ............. A61B 5/14532
                                                     600/347
2003/0100846 A1    5/2003  Custer

FOREIGN PATENT DOCUMENTS

GB         2461355 A       1/2010
WO    2016025468 A2       2/2016

* cited by examiner

*Primary Examiner* — Jennifer Wecker
*Assistant Examiner* — Michael Paul Shimek
(74) *Attorney, Agent, or Firm* — Jacob Eisenberg

(57) ABSTRACT

The application relates to a device (100) for non-invasively sampling interstitial fluid comprising one or more analytes from dermis (101 *a*) to skin surface (101 *b*) by using the magneto-hydrodynamic effect. The device comprises a first electrode (102*a*) and a second electrode (102*b*) adapted to be positioned adjacent to the skin surface, the first electrode separated from the second electrode by a distance (103), a power source (104) adapted to induce an electric current through the first electrode, the interstitial fluid and the second electrode, and also a magnet (105) adapted to produce a magnetic field to the interstitial fluid. Direction of the magnetic field and direction of the electric current produced by the magnet and the power source, respectively, is such that Lorentz force drives the fluid from the dermis towards the skin surface.

20 Claims, 3 Drawing Sheets

(51) Int. Cl.
- *G01N 33/66* (2006.01)
- *A61B 5/157* (2006.01)
- *A61B 5/145* (2006.01)
- *A61B 5/15* (2006.01)
- *A61B 5/00* (2006.01)
- *A61B 5/151* (2006.01)

(52) U.S. Cl.
CPC .......... *A61B 5/15134* (2013.01); *A61B 5/681* (2013.01); *A61B 5/7475* (2013.01); *G01N 33/66* (2013.01); *A61B 5/157* (2013.01); *A61B 5/150343* (2013.01); *A61B 5/6832* (2013.01); *A61B 2560/0214* (2013.01); *A61B 2560/0475* (2013.01)

(58) Field of Classification Search
CPC .......... G01N 30/88; G01N 2030/8831; A61P 31/12; A61P 27/02; A61P 11/00
See application file for complete search history.

DEVICE FOR SAMPLING ONE OR MORE ANALYTES

FIELD

This invention relates to devices based on magneto-hydrodynamics (MHD) to extract fluid comprising one or more analytes from a target, in particular, interstitial fluid from skin.

BACKGROUND

Interstitial fluid (IF) is an aqueous solution that serves as a transport medium for e.g. glucose and electrolytes between the cells and the circulatory system. Therefore, the concentration of different solutes, such as glucose and lactic acid, in IF and in blood exhibits a substantial correlation. This makes the analysis of IF relevant to many developing fields, including, medical diagnosis, early disease detection, pharmacokinetics, and smart wearable technologies. Furthermore, a strong commercial and scientific interest promotes research on painless and non-invasive IF sampling methods.

US2002/0002328A1 discloses a noninvasive IF device and method for sampling substances such as glucose through skin by reverse iontophoresis. The device is designed to monitor blood glucose levels in people with diabetes. The device is not considered a replacement, but an addition to conventional invasive blood glucose monitoring.

WO2010001122A2 discloses a patch for sampling one or more analytes through the skin of a patient. The patch comprises an electrode layer that is positioned adjacent to the skin of a patient, and means for actuating an electrode layer to induce the withdrawal of analyte through the skin by reverse iontophoresis. The patch comprises reservoir chambers containing an electrically conducting medium to induce the process of iontophoresis. According to the document, the presence of an electrolyte in liquid form ensures good conductivity between the electrodes and the skin, which enhances the effectiveness of the reverse iontophoresis process.

The state-of-the-art devices discussed above for noninvasive glucose monitoring are based on the harnessing of osmotic flow or electrophoresis. In these devices, the extraction occurs locally at the electrode-skin interface. Accordingly, a limited volume of fluid can be extracted and analyzed, which in turn requires sensitive detection and analysis techniques.

Thus, there is still need for further devices for sampling analytes through skin with improved efficacy and extraction rate.

SUMMARY

The present invention is based on the observation that at least some of the state-of-the-art problems related to sampling of one or more analytes from skin can be solved or at least alleviated by exploiting the magneto-hydrodynamic (MHD) phenomenon.

Accordingly, it is an object of the present invention to provide a device for sampling interstitial fluid comprising one or more analytes from dermis to skin surface in a non-invasive manner, the device comprising
- a first electrode and a second electrode adapted to be positioned adjacent to the skin surface, the first electrode separated from the second electrode by a distance,
- a power source adapted to induce electric current through the first electrode, the interstitial fluid and the second electrode, and
- one or more magnets adapted to induce magnetic field to the interstitial fluid.

According to the device of the present invention direction of the magnetic field produced by the one or more magnets, and direction of the electric current produced by the power source is adapted to be such that Lorentz force produced by the magnetic field and the electric current is adapted to drive the interstitial fluid from the dermis substantially towards the skin surface.

According to the device of the present invention, the IF can be sampled from the skin not only locally at the electrode-skin interface as in the state of the art, but also between the electrodes, where a further volume of IF is available. Furthermore, MHD adds a force component that increases the extraction rate under a negative electrode.

Further objects of the present invention are described in the accompanying dependent claims.

Exemplifying and non-limiting embodiments of the invention, both as to constructions and to methods of operation, together with additional objects and advantages thereof, are best understood from the following description of specific exemplifying embodiments when read in connection with the accompanying drawings.

The verbs "to comprise" and "to include" are used in this document as open limitations that neither exclude nor require the existence of un-recited features. The features recited in the accompanied depending claims are mutually freely combinable unless otherwise explicitly stated. Furthermore, it is to be understood that the use of "a" or "an", i.e. a singular form, throughout this document does not exclude a plurality.

DESCRIPTION

According to one embodiment, the present invention concerns a device for sampling IF in a non-invasive manner. The IF comprises one or more analytes to be analyzed. According to the invention, the IF is extracted from the skin by exploiting the MHD phenomenon.

Figure 1:
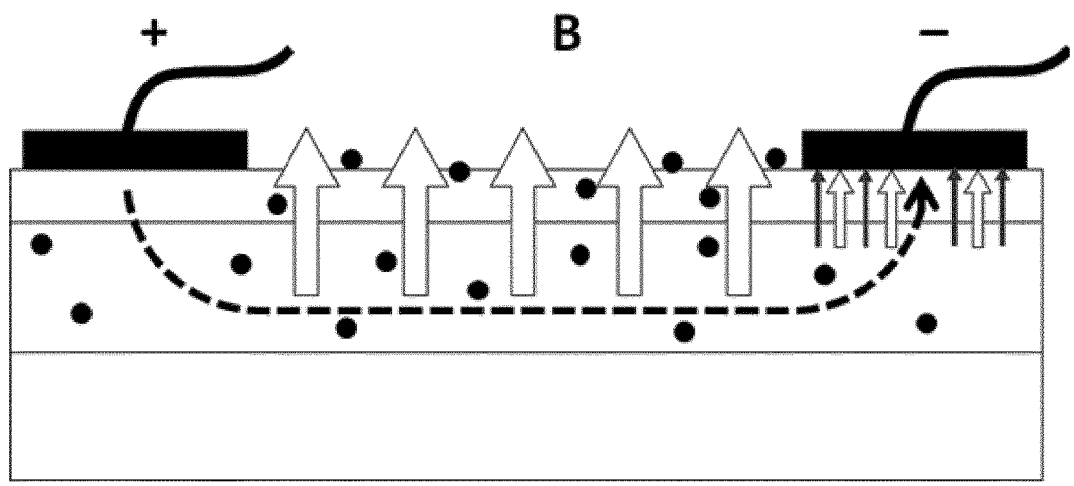
FIG. 1 illustrates the principle of the device according to the present invention for sampling e.g. extracting an analyte such as glucose (black dots) from skin; (+): the first electrode; (−): the second electrode; dotted arrow: direction of electric current; (B): magnetic field; upper layer: the epidermis; middle layer: dermis; lower layer: hypodermis; white arrows: fluid displacement in the direction of the Lorentz force; black arrows: direction of electrophoresis.

FIG. 1 shows the working principle of the present invention. In the figure, the device serves to extract IF from skin. Accordingly, an electric current produced by a power source is established through a pair of electrodes (marked with + and −) and the skin. The magnetic field (B) is produced by a magnet. The current density in the middle skin layer (dermis) is substantially higher than in the inner (hypodermis) or outer (epidermis) skin layers because the higher content of IF in the dermis offers a lower impedance electric path. When the device is in operation, the direction of the magnetic field is substantially perpendicular to the skin surface, particularly within the distance and at the location of the electrodes, and substantially perpendicular to desired direction of fluid displacement from the dermis to the skin surface. Therefore, the current-carrying fluid in the magnetic field experiences a Lorentz force towards the skin surface. This force serves to drive IF out of the skin. The driving force exerted in the fluid is described by the equation $F=J \times B$; where F, J, and B are the force, current density, and magnetic field vectors respectively, and × indicates a cross product. Based on this equation, the vectors of Lorentz force, electric current, and magnetic field are all perpendicular to each other. Also, the force distribution is defined by the distribution of the electric current and the magnetic field. The distribution of Lorentz force in the current carrying fluid permits directional driving of the IF out of the skin along the whole/entire current path i.e. along the distance between the electrodes. The fluid displacement in the direction of the Lorentz force is indicated with white big arrows. The IF containing relevant analytes, such as glucose, shown as black dots in the figure, is extracted also along the distance between the electrodes and not only under the negative electrode wherein also electrophoresis (black small arrows) promotes movement of fluid towards the electrode-skin interface.

Figure 2:
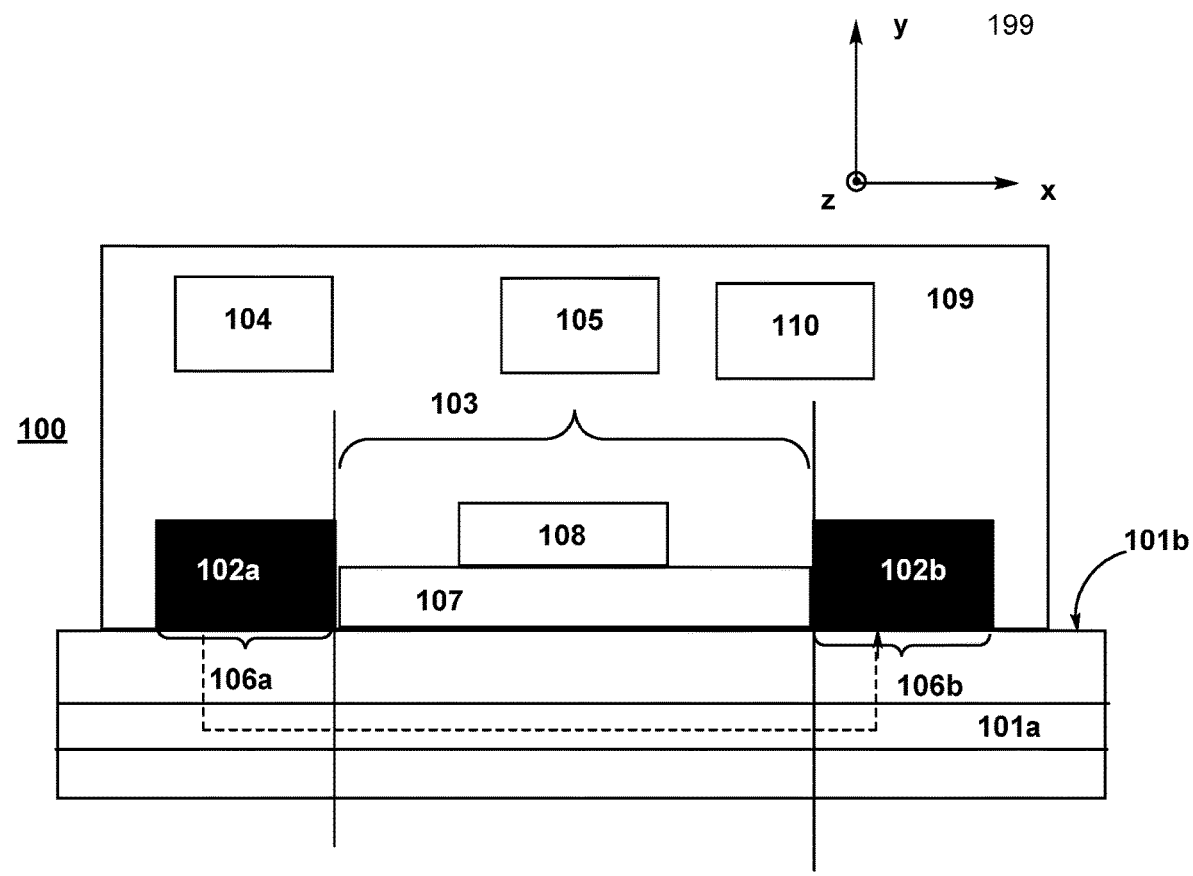
FIG. 2 illustrates an exemplary non-limiting device according to the present invention.

An exemplary device according to the present invention is shown in FIG. 2. Accordingly, a device 100 for sampling IF comprising one or more analytes from dermis 101a to skin surface 101b comprises a first electrode 102a and a second electrode 102b adapted to be positioned adjacent to the skin surface, the first electrode separated from the second electrode by a distance 103, a power source 104 adapted to induce an electric current through the first electrode, the interstitial fluid and the second electrode, and a magnet 105 adapted to induce a magnetic field to the interstitial fluid, wherein direction of the magnetic field produced by the magnet and direction of the electric current produced by the power source is such that that Lorentz force is adapted to drive the interstitial fluid from the dermis substantially towards the skin surface along the entire current path, in particular within the distance and the (−)-electrode.

When the device is in operation, the electric current flows substantially in three different directions as described by the dotted arrow in FIG. 2: initially from the first electrode towards the skin, in particular towards the dermis comprising the IF, then within the distance between the electrodes, substantially parallel to the skin surface, and finally from the dermis towards the second electrode (i.e. the (−)-electrode), i.e. in −y-, x- and y-directions, respectively of the coordinate system 199 of FIG. 2. Accordingly, the electric current contributes to driving a certain volume of IF towards the second electrode.

In order to produce a Lorentz force in the current-carrying IF in the skin towards the skin surface, the magnet should produce a magnetic field that is substantially in z-direction of the coordinate system 199. Accordingly, the MHD effect produced by the magnetic field and the electric current drives the IF comprising the one or more analytes from the dermis substantially towards the skin surface within the distance and below the (−)-electrode 102b. Accordingly, the direction of the flow of the IF is substantially in y-direction of the coordinate system 199.

According to an exemplary embodiment the first electrode, and the second electrode is a silver-silver chloride (Ag—AgCl) electrode to avoid electrolysis of water and pH drifts. However, other inert and non-ferromagnetic materials are also suitable. Exemplary further materials are carbon, gold, and platinum.

The electrodes can be coated with different materials, for instance, enzymes and catalysts such as glucose oxidase, dehydrogenase and Prussian blue. Furthermore, different materials or combination of materials can be used as an interface between the electrodes and the skin for instance to reduce the electric impedance, to protect the electrode coating and to facilitate the analysis of the extracted IF samples. Suitable materials for this purpose include biocompatible membranes (i.e. permeable or semipermeable) made of regenerated cellulose, silicone and monofilament fabric of polyamide.

The interface serves to maintain a low electric impedance between the electrodes and the skin, to facilitate the transport of analytes towards the device, to preserve electrochemical conditions (e.g. pH) and activity of the enzyme. In one embodiment, the electrode skin interface is preferable a gel or hydrogel. In another preferred embodiment, the electrode skin interface is a membrane which is permeable or semipermeable, electrically conductive, and hypoallergenic. Exemplary materials suitable for this purpose include biocompatible membranes (i.e. permeable or semipermeable) made of regenerated cellulose, silicone and monofilament fabric of polyamide. These membranes can be treated with agents that work as humectants (i.e. glycerol, agarose gel and phosphate buffered saline) to help maintain the desired pose structure and to increase its electric conductivity. The membranes can also be loaded with agents, such as corticosteroids and other drugs, to prevent or reduce potential skin reactions induced by the extraction procedure.

According to the exemplary embodiment shown in FIG. 2, the first electrode 102a is acting as a positive electrode and the second electrode 102b is acting as a negative electrode. It is to be understood that the polarity of the electrodes can be flipped and that other configurations are possible. The first electrode and the second electrode are preferably substantially parallel to each other. The device may include plurality of first electrodes and plurality of second electrodes. The electrodes can be same of different.

The first electrode and the second electrode comprise a contact surface. The contact surfaces are shown in FIG. 2 with reference numbers 106a and 106b for the first electrode and the second electrode, respectively. According to one exemplary embodiment, the contact surface of the electrodes is flat and either circular e.g. disk-shaped, rectangular, elliptical or pyramidal. According to another embodiment the contact surface is adapted to the shape of the skin surface. For example, if the skin is in a finger or in the wrist, the contact surface may be substantially curved to allow maximal mechanical and electric contact with the skin. The contact surface may comprise extrusions and/or protrusions to facilitate maximal adherence to the skin surface.

The area of the contact surface of each electrode is preferably between 0.01 cm$^2$ and 9 cm$^2$, and most preferably between 0.15 cm² and 1 cm². The distance between the first electrode and the second electrode is preferably between 1 mm and 5 cm, and most preferably between 5 mm and 3 cm. According to an exemplary embodiment the distance is 1 cm.

Figure 3:
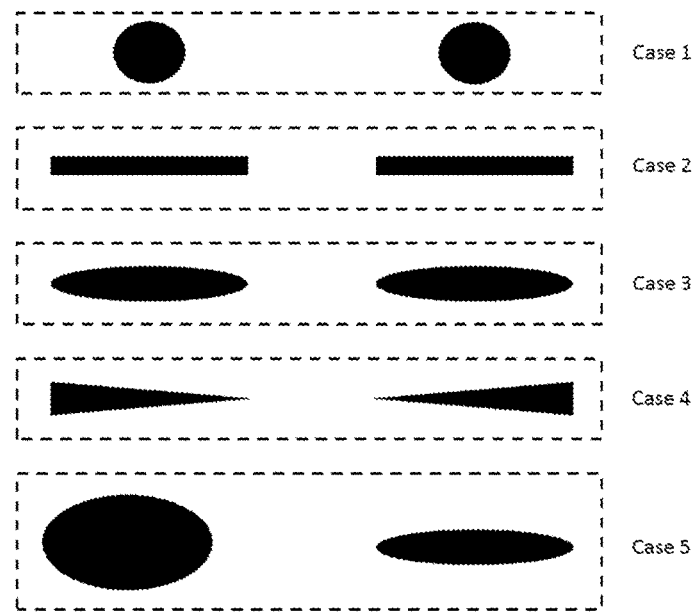
FIG. 3 illustrates exemplary non-limiting electrode shapes.

According to one embodiment, the shape of the contact surface of the electrodes is elliptical, and the major axis of the ellipsis is substantially larger than the minor axis. This allows to set a larger current density through the dermis without increasing the current density at the electrode-skin interface. Exemplary electrode shapes are shown in FIG. 3. This figure depicts five cases illustrating different electrode configurations (first electrode to the left, and second electrode to the right). The current density through the target such as skin can be different in all cases even if the contact area of the electrodes is the same. The electrode shape can alter the distribution of electric current in the skin, and therefore, the local current density to increase the Lorentz force and the extraction rate of IF. For this reason, the elliptical electrode shapes illustrated in case 3 are preferable.

The power source 104 can be a direct current (DC) power source and/or an alternating current (AC) power source that limits and regulates the energy i.e. the intensity of the electric current and/or voltage delivered through the electrodes. According to an exemplary embodiment, the power source is a floating current source that provides means to establish a direct electric current preferably in the range of 10 µA to 10 mA, and more preferably in the range 0.1 mA to 1 mA. The current density at the electrode-target, such as skin interface is preferably between 1 µA/cm² and 10 mA/cm², and most preferably between 0.1 mA/cm² and 1 mA/cm². The voltage provided by the current source is preferable between 1 and 100 V.

In a particular embodiment, the electric current established by the floating current source exhibits a unipolar (unidirectional) or bipolar (e.g. bidirectional or alternating) waveform. The frequency of the electric signal is preferably between 0.1 Hz and 100 kHz, and more preferably between 10 Hz and 10 kHz. The electric signal can be modulated in amplitude and/or frequency, and can have different waveforms, for instance, sine, square, pulsed (e.g. rectangular), triangle, and saw tooth. Also, the signal can be burst- and/or duty-cycle-modulated.

The magnet 105 can be a permanent magnet or an electromagnet. The intensity of the magnetic field at the surface of the magnet is preferably between 0.01 mT and 2 T, and most preferably between 0.1 mT and 500 mT. The distance between the magnet and the electrodes is preferably less than 5 cm, more preferably less than 3 cm, and most preferably less than 1 cm. According to an exemplary embodiment, the magnetic field is provided by a neodymium magnet located 0.5 cm apart from the skin surface when the device is at its operational position. Also, when the device is at its operational position, the direction of the magnetic field is substantially perpendicular to the skin surface within the distance and substantially perpendicular to desired direction of fluid displacement from the dermis to the skin surface. Consequently, the dermal IF is driven towards the surface of the skin.

According to another embodiment the device comprises plurality of magnets. According to an exemplary embodiment, the magnetic field is provided by an array of magnets or electromagnets. An exemplary array is a Halbach array 211 shown in FIG. 4. Two of the magnets are shown with the reference numbers 205a and 205b. The overlapping magnetic fields of the magnets in the array combine to produce a resultant magnetic field acting in one direction marked with the letter B. The electrodes (not shown) are positioned inside the array so that the electric field E is as shown in the coordinate system 299. Accordingly, the direction of IF extraction can be adapted to be towards the skin surface.

The use of arrays of magnets allows to modulate (i.e. to augment, decrease or cancel) the magnetic field directionally or locally. For instance, a circular Halbach array consisting on a cylinder composed of neodymium magnets can be used to produce an intense magnetic field confined within the cylinder. Moreover, the array of magnets can be positioned wrapping the electrode and the extraction site, for instance in a ring or wristband, where the electrodes are arranged inside the cylinder. This allows having a strong magnetic field at the extraction site while keeping a week magnetic field elsewhere.

According to one embodiment the device comprises means 107 adapted to store (e.g. to collect) and/or means 108 adapted to analyze the IF comprising one or more analytes extracted from the skin. According to an exemplary embodiment, the storing means comprises one or more capillaries located within the distance 103. The one or more capillaries are preferably coaxial with the electrodes, and one end of the capillaries is located so that the IF extracted from the skin moves into the one or more capillaries. According to a particular embodiment, the means adapted to store the fluid, such as the one or more capillaries or a reservoir, act also as means adapted to transfer the fluid to means 108 adapted to analyze the one or more analytes. Alternatively, the means 108 is adapted to record one or more signals derived from the one or more analytes and to send the one or more signals to means adapted to analyze them. According to an exemplary embodiment, the means 107 and/or 108 comprises medium such as gel or liquid comprising glucose oxidase adapted to form hydrogen peroxide, the concentration of which is determined electrochemically and/or optically. The means 107 and 108 are preferably located within the distance and/or under one or more electrodes. According to another embodiment, the device comprises means for storing and analyzing interstitial fluid. According to still another embodiment, the analyzing means is separated from the device.

According to an exemplary embodiment, the device comprises a frame 109 adapted to position the electrodes, the power source, and the magnet, and any further means of the device such as the energy storing means (such as a battery), the IF storing means and the IF analyzing means. The contact surface of the first electrode, the contact surface of the second electrode, and preferably also the means adapted to store and/or analyze the one or more analytes are on the surface of the frame adapted to be in direct or indirect contact with the skin surface.

According to another embodiment the frame of the device is of pocket size.

According to an exemplary embodiment, the MHD device of the present invention is combined with other approaches, such as sonoporation, laserporation, electroporation and hydraulic pressure, to increase the permeability of the skin. The different permeability-enhancing approaches can be used to disrupt the mechanical properties of the upper layer of the skin (e.g. the stratum corneum) temporarily or permanently. This can facilitate the IF extraction. For instance, sonoporation can be applied before or during IF extraction with the device of the present invention (e.g. constantly or recurrently). Accordingly, the device of the present invention may comprise one or more means 110 selected from ultrasound generating means, laser light generating means, electroporation generating means, hydraulic pressure generating means.

Figure 4:
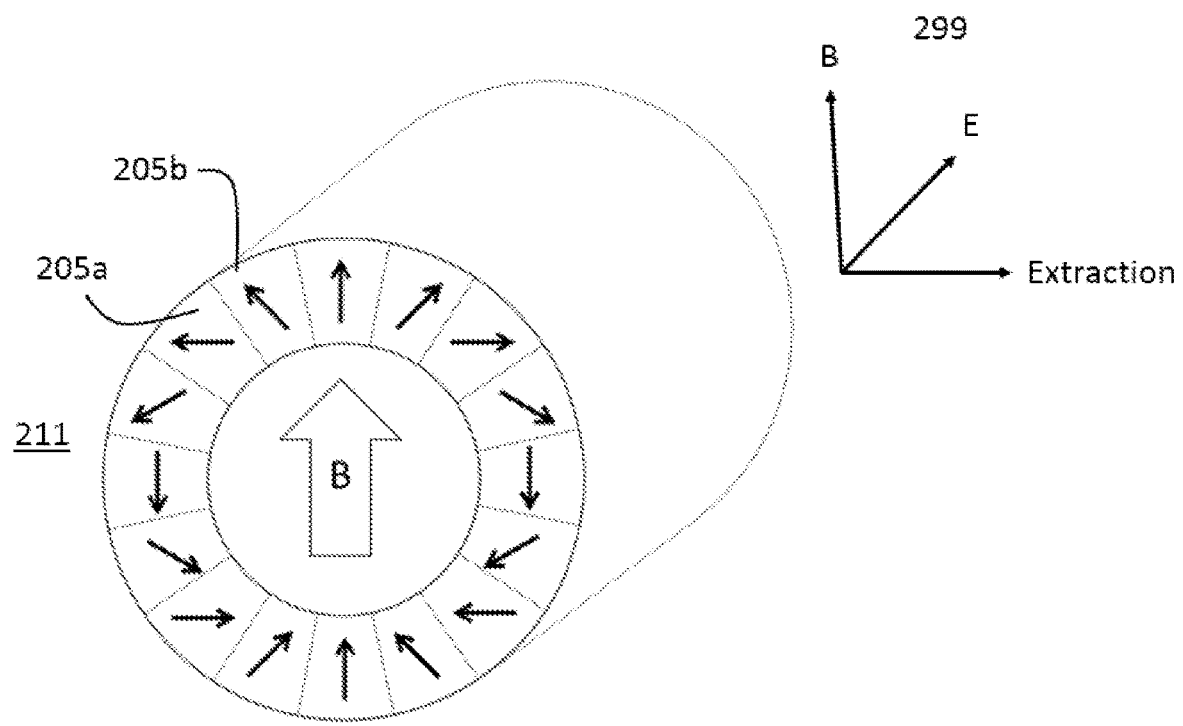
FIG. 4 illustrates an exemplary magnet array suitable for use in the device according to the present invention.
Figure 5:
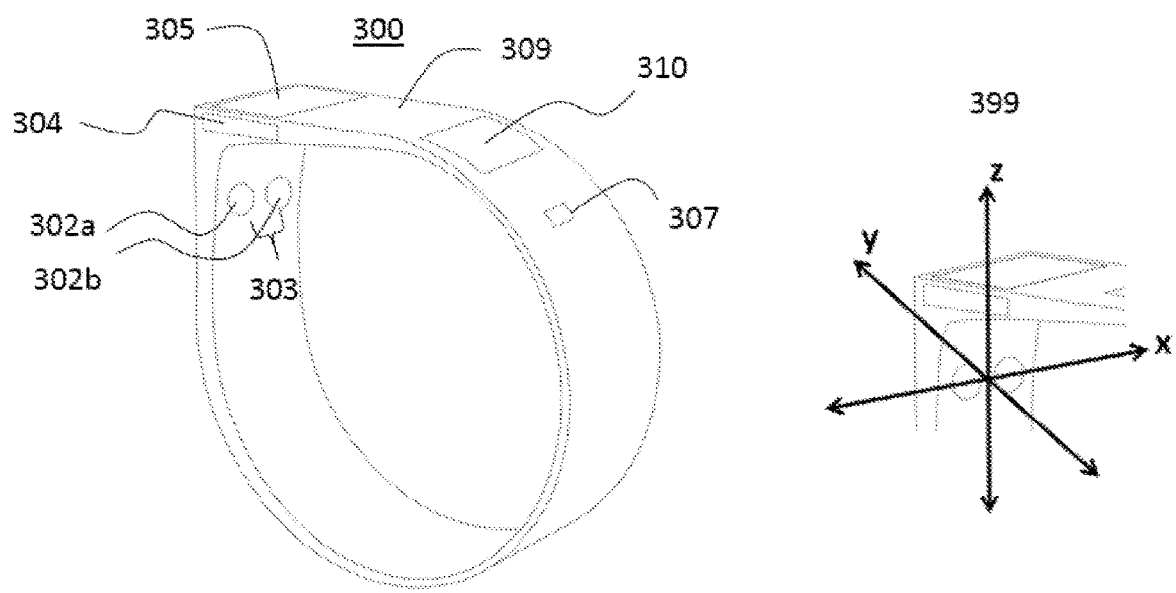
FIG. 5 illustrates a schematic view of a non-limiting exemplary device in form of a wristband according the present invention.

Another exemplary non-limiting device 300 according to the present invention is shown in FIG. 5. Frame of the device is in form of a wristband 309. The device shown therein comprises a first electrode 302a and a second electrode 302b adapted to be positioned adjacent to skin surface. The first electrode and the second electrode are separated by a distance 303. The device comprises also a power source 304 adapted to induce an electric current through the first electrode, interstitial fluid and the second electrode when the device is at its operational position. The device comprises also a magnet 305 adapted to induce a magnetic field to the IF. Direction of the magnetic field and direction of the electric current is such that Lorentz force is adapted to drive the IF from dermis substantially towards the skin surface. The magnetic field can also be produced by a plurality of magnets, such as an array of magnets as shown in FIG. 4.

In order to produce Lorentz force in the current-carrying IF in the skin within the distance and below the negative electrode towards the skin surface, the magnet 305 should produce a magnetic field that is substantially in z-direction of the coordinate system 399. Accordingly, the MHD effect generated by the magnetic field produced by the magnet 305 or plurality of magnets and the electric current established by the power source 304 drives the IF comprising the one or more analytes from dermis substantially towards the skin surface. Accordingly, the direction of the flow of the IF is substantially in y-direction of the coordinate system 399. The location of the power source and the magnet in FIG. 5 are only illustrative.

The advantages of this embodiment are that the wristband can offer means to position the first electrode and the second electrode in contact with the skin, for instance, by using adhesive materials, pneumatic force and/or mechanical pressure. According to the embodiment shown in the figure, a permanent magnet is arranged in the wristband close to target site of interstitial fluid extraction, so that the magnetic field is substantially perpendicular to the skin surface within the distance and substantially perpendicular to the direction of fluid from the dermis to the skin surface. To accomplish this, the wristband may have movable parts such as a retractable magnet holder. Furthermore, the wristband can offer means to collect, transport, store and/or analyze the interstitial fluid sample (not shown in FIG. 5). Also, the wristband can be provided with an electronic or electro mechanical user interface comprising, for instance, a display 310, such as a touch screen display, push buttons, and mechanical, visual and/or audio indicators (e.g. light emitting diodes, loudspeaker and vibrating alarms). Furthermore, the wristband may have means to store data such as an electronic circuit and means to send data, preferably wirelessly, to another electronic device such as a cellphone, a tablet, a computer or an insulin pump. Also, the device may have means to connect to Internet. An electronic circuit in the wristband can also serve to monitor the electric current and/or voltage applied to the skin to assess the electrode-skin electric contact. The energy required for the operation of the electronic circuit can be provided by, for instance, a rechargeable battery adapted in the wristband. In one particular embodiment of the invention, the wristband encompasses one or more capillaries made of organic or inorganic materials (e.g. polyfluorocarbon, polyethylene, polyvinyl chloride, and borosilicate glass) to collect the interstitial fluid sample. The tip of the capillaries is arranged close to, or in contact with, the extraction site. For instance, they can be arranged in the electrode gap and/or integrated in the first electrode and/or in the second electrode. Other suitable elements to collect the extracted IF samples or compounds in the IF samples include electrically and/or magnetically charged materials, hydrophobic and/or hydrophilic materials, and absorbent materials. In another particular embodiment of the invention, the electrodes are coated with a substance or mixture that reacts (e.g. chemically or physically) or that binds to one or more constitutes of the IF sample. Exemplary electrode coatings include gels, such as hydrogels and polymeric gels, where the gels can be further loaded with reagents such as enzymes, for instance, glucose oxidase. The electrode coating can serve to collect the sample of interstitial fluid or particular components of the sample and to allow further sample analysis, for instance, to measure the content of glucose, lactic acid or other compounds in the IF sample by applying current technologies or technologies developed in the future. Also, in humans, this invention can also be implemented in different parts of the body, including (but not limiting to) the head, earlobe, eyes, neck, nose, mouth, chest, abdomen, arms, forearms, legs, fingers (e.g. as in a ring), feet, and toes. Furthermore, the invention can be used in any living or dead biological organism, including but not limiting humans and animals (e.g. in the ears, legs, or in the tail of dogs or rats).

The device of the present invention is suitable for sampling one or more analytes that can be withdrawn from skin by using the MHD phenomenon. Exemplary non-limiting analytes comprise amino acids, sugars, fatty acids, co-enzymes, hormones, neurotransmitters, lactic acid, and drugs. A particular analyte is glucose. Another particular analyte is lactic acid.

EXAMPLES

Example 1

The efficacy of the device according to the present invention to extract dermal IF was compared to electrophoresis. Postmortem abdominal porcine skin samples (3 cm×3 cm) dissected from adjacent tissue were treated with 1) the device according to the present invention and 2) the device according to the present invention but omitting the magnetic field. Accordingly, in experiment 1) and experiment 2) the sampling was performed by MHD and electrophoresis, respectively.

Figure 6:
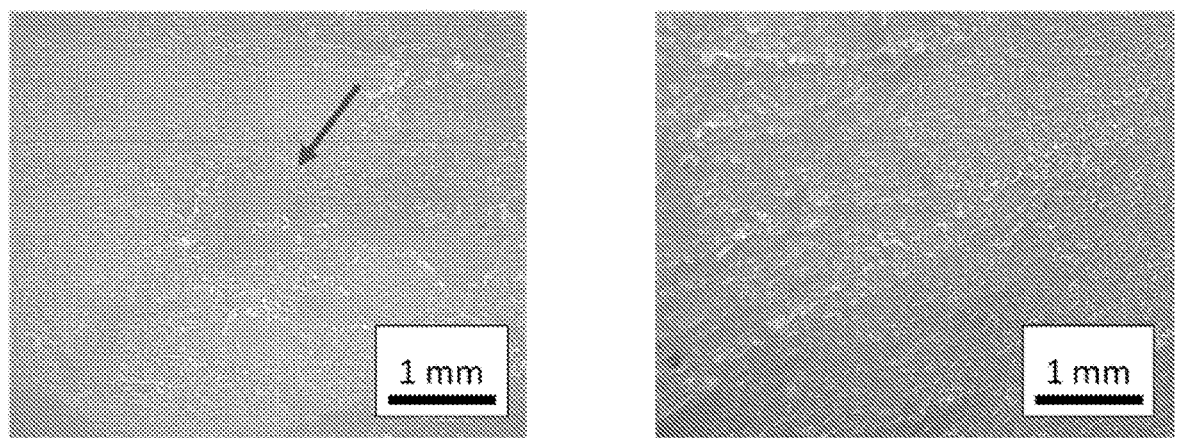
FIG. 6 illustrates result of treatment of a skin sample using an exemplary device of the present invention (MHD to the left) and by using a device according to state of the art (electrophoresis to the right).

The two experiments were run simultaneously and applying the same parametrization and electrode configuration. In each case, the first electrode and the second electrode were made of graphite. The contact surface of all the electrodes was flat and round (diameter=7 mm). A single current source was used to establish a 0.4 mA direct electric current serially in the two treatments. The estimated current density at the electrode-skin interface was 1 mA/cm$^2$. The separation between the first electrode and the second electrode in both experiments was 1 cm. For the device according to the present invention exclusively, a permanent neodymium magnet with a 0.8 T magnetic field at its surface was arranged at distance of 1 cm from the extraction site. The magnet was arranged in such a way that the magnetic field was established in a direction substantially perpendicular to the skin surface within the distance and substantially perpendicular to desired direction of fluid displacement from the dermis to the skin surface. Consequently, a Lorentz force was generated towards the skin surface in the current-carrying fluid in the skin. An exposure-to-treatment time of 1 hour revealed a clear difference in the volume of dermal IF extracted by the two methods. As seen in FIG. 6, the fluid extracted with the device according to the present invention forms a drop (marked with an arrow in FIG. 6, left) that can be seen by the naked eye and whose volume is substantially larger than the volume of fluid extracted by electrophoresis, which is not sufficiently large to be distinguished by the naked eye. Considering that the extracted fluid is subject to evaporation, the accumulation of fluid observed in the sample treated with the device according to the present invention is a strong indicator that this method is substantially faster than electrophoresis.

Example 2

The concentration of glucose in intestinal fluid and blood was measured by using a device according to the present invention and by using a conventional fingertip pricking instrument in a group of healthy adult humans (n=11).

For each measurement, paired samples of interstitial fluid and blood were concurrently obtained using either the device according to the present invention or conventional fingertip pricking instrument (CareSensTMN; model GM505PAD, i-SENSm inc, Seoul, Korea), respectively. The concentration of glucose in the samples of interstitial fluid was measured using a commercial assay kit (AB65333, Abcam Cambridge, UK). The results showed a direct relationship between the concentration of glucose in the samples of interstitial fluid and blood. The results confirm that the concentration of glucose in the samples extracted with a device according to the present invention can be used to estimate blood glucose. Furthermore, no pain, skin reactions, or evident sample disruption was induced by the extraction procedure.

The concentration of glucose in interstitial fluid correlates with the concentration of glucose in blood. In one preferred embodiment, once the concentration of glucose in the sample of interstitial fluid is measured, a mathematical algorithm or mathematical model can be used to estimate the corresponding level of blood glucose. This mathematical algorithm can consist of arithmetic operations, statistical functions and even artificial intelligence algorithms.

Further embodiments are disclosed in the following numbered clauses.

1. A method for sampling interstitial fluid comprising one or more analytes from dermis to skin surface, the method comprising steps of:
   positioning a first electrode and a second electrode adjacent to the skin surface,
   inducing an electric current through the first electrode, the interstitial fluid and the second electrode, and
   inducing a magnetic field to the interstitial fluid comprising the one or more analytes, wherein direction of the magnetic field and the electric current is such that Lorentz force drives the interstitial fluid from the dermis substantially towards the skin surface.

2. The method according to clause 1 comprising treating the skin surface by one or more of: ultrasound, laser light, hydraulic pressure, electric field.

3. The method according to clause 1 or 2 comprising storing and/or collecting the interstitial fluid comprising the one or more analytes sampled from skin.

4. The method according to clause 1 or 2 comprising transporting the interstitial fluid comprising one or more analytes withdrawn from skin to a location where the one or more analytes are analyzed.

5. The method according to any or clauses 1-4, wherein the one or more analytes comprises amino acids, sugars, fatty acids, co-enzymes, hormones, neurotransmitters, lactic acid, drugs.

6. The method according to any of clauses 1-5 wherein the analyte is glucose, proteins, and/or lactic acid.

7. The method according to any of clauses 1-6, wherein the method further comprises analyzing the one or more analytes.

The specific examples provided in the description given above should not be construed as limiting the scope and/or the applicability of the appended claims.

What is claimed is:

1. A device for sampling interstitial fluid comprising one or more analytes from dermis to skin surface, the device comprising:
   a first electrode and a second electrode adapted to be positioned adjacent to the skin surface, the first electrode separated from the second electrode by a distance,
   a power source adapted to induce an electric current through the first electrode, an interstitial fluid and the second electrode,
   one or more magnets adapted to induce magnetic field to the interstitial fluid, and
   in that a direction of a magnetic field produced by the one or more magnets, and a direction of an electric current produced by the power source are adapted so that a Lorentz force produced by the magnetic field and the electric current is adapted to drive the interstitial fluid from a dermis substantially towards the skin surface.

2. The device according to claim 1 further comprising a frame adapted to position the first electrode, the second electrode, the power source and the one or more magnets.

3. The device according to claim 1, wherein the first electrode and the second electrode are adapted to be substantially perpendicular to the skin surface when the device is at an operational position.

4. The device according to claim 1, wherein the distance between the first and second electrode is 1 mm-5 cm.

5. The device according to claim 1, wherein the device further comprises a means adapted to collect, store or collect and store one or more analytes sampled from the dermis.

6. The device according to claim 5 wherein the device further comprises a means adapted to analyze the one or more analytes.

7. The device according to claim 1, wherein a contact surface of the first electrode and/or a contact surface of the second electrode is elliptical.

8. The device according to claim 1, wherein a contact surface of the first electrode and/or a contact surface of the second electrode includes extrusions and/or protrusions.

9. The device according to claim 2, wherein the frame is in form of wristband or a ring.

10. The device according to claim 9, wherein the frame is in a from of a wristband, and the wristband includes one or more of the following: a user interface, a means adapted to store data, a means adapted to send and receive data, and a means adapted to provide energy to the power source.

11. The device according to claim 1, further comprising a means selected from one or more of the following: an ultrasound generating means, a laser light generating means, an electroporation generating means, and a hydraulic pressure generating means.

12. The device according to any of claim 2, wherein the frame includes an adhesive material adapted to be positioned in contact with the skin.

13. The device according to claim 1, wherein the first electrode and/or the second electrode is coated with one or more enzymes and/or one or more catalysts.

14. The device according to claim 1, wherein the device further comprises a membrane and/or an electrically conducting material adapted to be positioned between the first electrode and the skin, and between the second electrode and the skin.

15. A method for sampling interstitial fluid comprising one or more analytes from dermis to skin surface, the method comprising steps of:
positioning a first electrode and a second electrode adjacent to the skin surface,
inducing an electric current through the first electrode, the interstitial fluid and the second electrode, and
inducing a magnetic field to the interstitial fluid comprising the one or more analytes, wherein a direction of the magnetic field and the electric current is such that a Lorentz force drives the interstitial fluid from the dermis substantially towards the skin surface.

16. The method according to claim 15 further comprising treating the skin surface by one or more of: an ultrasound, a laser light, a hydraulic pressure and an electric field.

17. The method according to claim 15 further comprising storing and/or collecting the interstitial fluid including one or more analytes sampled from skin.

18. The method according to claim 17 further comprising transporting the interstitial fluid comprising one or more analytes withdrawn from skin to a location where the one or more analytes are to be analyzed.

19. The method according to claim 17, wherein the one or more analytes includes amino acids, sugars, fatty acids, co-enzymes, hormones, neurotransmitters, lactic acid or drugs.

20. The method according to claim 15, wherein the method further comprises analyzing the one or more analytes.

* * * * *